6/9/81    XR    4,271,706

United States Patent [19]
Ledley

[11] 4,271,706
[45] Jun. 9, 1981

[54] ULTRASONIC SCANNER

[75] Inventor: Robert S. Ledley, Silver Spring, Md.

[73] Assignee: Georgetown University, Washington, D.C.

[21] Appl. No.: 902,740

[22] Filed: May 3, 1978

[51] Int. Cl.³ .............................................. G01N 29/00
[52] U.S. Cl. ..................................... 73/614; 73/620; 128/660
[58] Field of Search .......... 128/2 V, 2.05 Z, 660–663; 340/5 H, 5 MP; 343/7.9; 73/603–605, 610–616, 631, 640, 609, 618–620, 634

[56] References Cited

U.S. PATENT DOCUMENTS

| | | | |
|---|---|---|---|
| 3,334,622 | 8/1967 | Brech | 128/2 V |
| 3,751,976 | 8/1973 | Pike | 73/614 X |
| 3,778,757 | 12/1973 | Houston | 340/5 MP |
| 3,792,423 | 2/1974 | Becker et al. | 340/5 MP |
| 3,832,887 | 9/1974 | Zeutschel | 73/610 X |
| 3,881,466 | 5/1975 | Wilcox | 128/2 V |
| 3,918,297 | 11/1975 | Rocha | 73/612 X |
| 4,021,771 | 5/1977 | Collins et al. | 340/5 MP |
| 4,070,643 | 1/1978 | Green | 340/5 H |
| 4,131,022 | 12/1978 | Mezrich | 128/2 V X |
| 4,135,406 | 1/1979 | Kretz | 73/620 |

FOREIGN PATENT DOCUMENTS 2060269  6/1972  Fed. Rep. of Germany ............ 128/660

OTHER PUBLICATIONS

Wells, P.N.T., *Biomedical Ultrasonics*, Academic Press, 1977.
Christensen, E. E. et al., *An Introduction to the Physics of Diagnostic Radiology*," Lea & Febiger, Philadelphia, 1978, pp. 361–394.
Goldberg, Barry E., *Abdominal Gray Scale Ultrasonography*, pp. 1–17.

*Primary Examiner*—Robert W. Michell
*Assistant Examiner*—Francis J. Jaworski
*Attorney, Agent, or Firm*—Larry S. Nixon

[57] ABSTRACT

An ultrasonic pulse is directed into a body and electrical representations of pulse reflections from body interfaces along its path are generated. The ultrasonic signal path is scanned through a volume of the body and position signals indicative of the instantaneous path disposition are generated. The reflection signals are selectively gated in accordance with a predetermined function of the path disposition to provide a display selectively representing desired interfaces situated within a selected contoured portion of the volume. By varying the predetermined function, a specific desired interface surface may be displayed. Provisions for developing a three dimensional display of the selected surface are described.

25 Claims, 7 Drawing Figures

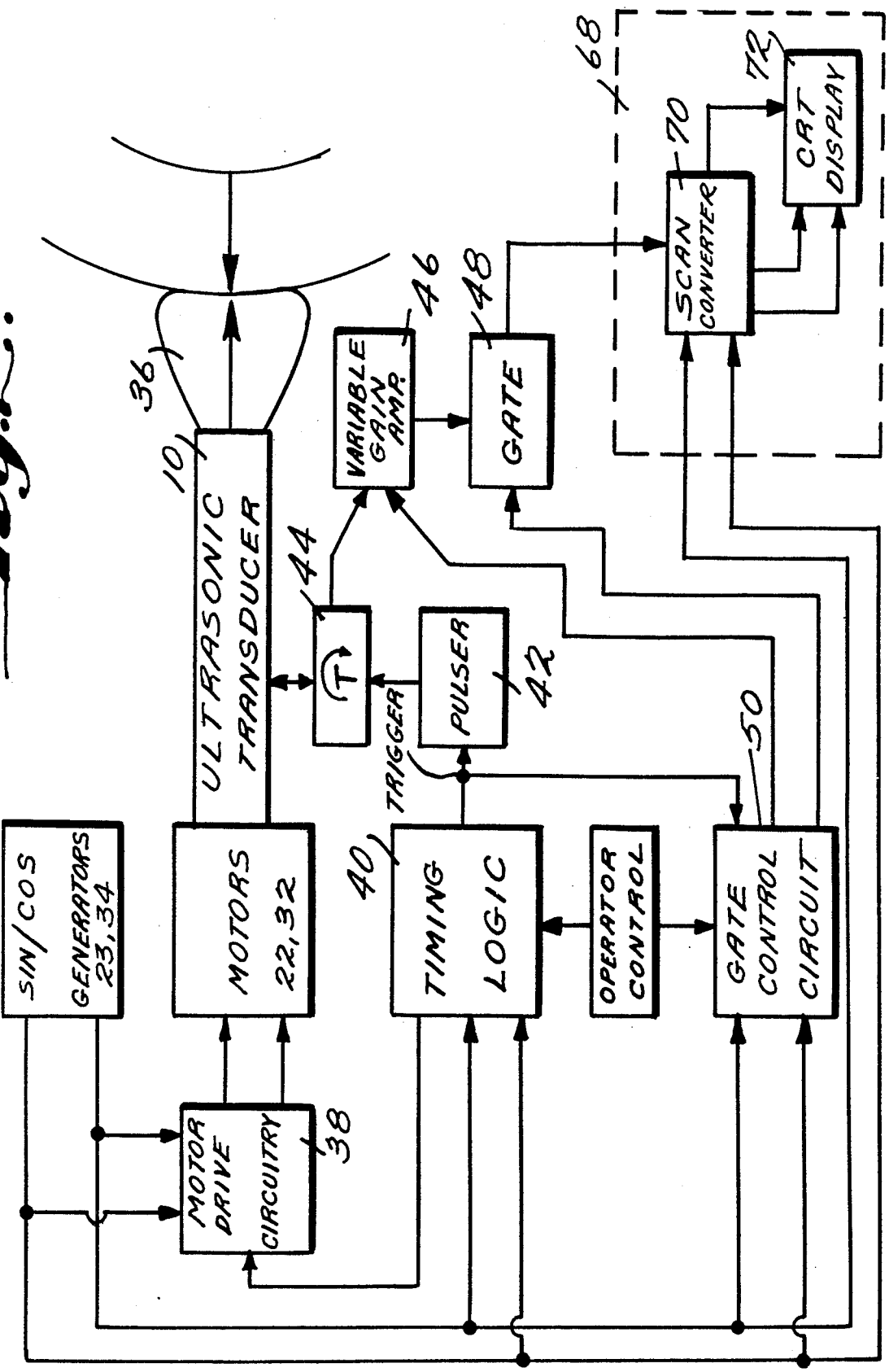

ULTRASONIC SCANNER

The present invention is directed to an ultrasonic scanning system for displaying an interface or surface located within a body, and particularly to such an ultrasonic scanner for use as a medical instrument.

Ultrasonic scanning systems of various types are well known in the prior art. For example, most prior art medical ultrasonic scanning systems generally utilized may be classified as A-type or B-type. In an A-type scanner, a fixed transducer provides an ultrasonic pulse which is directed along a fixed path into the body. The time-of-return for reflections from internal organic interfaces are detected to provide an indication of the distance to such interfaces. In a B-type scanner, a pulsed ultrasonic beam is swept in a single direction, and, as in the A-type scanner, the successive distances (ranges) to reflecting organic interfaces are determined by standard intervalometer methods. These B-type scanners typically provide an indicia of the interface by, in effect, plotting the detected distances against the position of the beam path. Various B-type scanners have included a real time display and have effected scanning electrically, for example, by use of a phased transducer array.

In the present invention, a volume is scanned in two dimensions and the three-dimensional contours of an interface surface are depicted on a two-dimensional display. Selective range gating, in accordance with a predetermined and/or variable function of the instantaneous scan position, is utilized to select and contour the volume actually depicted within the display. Such selective contouring eliminates "hash" or "clutter" reflections from interfaces other than that of interest. For example, in terms of a Cartesian coordinate system, assuming the Z axis to be pointed into the body and the scan performed in the X, Y plane, the gating circuits selectively pass reflections from interfaces located within a range of Z coordinates determined as a function of the X and Y position of the signal path.

It is noted that in the human body, most organs are roughly spherical in shape. Accordingly, it has been found more convenient in a medical environment to operate in a polar coordinate system, in effect, raster-scanning a solid angle within the body. The scanning operation is then described in terms of the angular disposition of the signal path defined by the angles $\alpha$ (with respect to the X direction) and $\theta$ (with respect to the Y direction) and the radial distance R from the transducer. The gating function is performed in the radial direction.

Such selective gating allows for a display showing only the surface of a desired interface. Further, the scanning function can be varied by an operator to fit the shape of a particular surface.

It has now been recognized by the present inventor that the magnitude (intensity) of the reflection from an interface is a function of the angle of the beam with respect to a tangent plane or normal line to the reflecting surface. When the angle of incidence between the beam and a normal line is small, the itensity of retro-reflection is high. Conversely, when the angle between the beam and a normal line is large, the retro-reflection is of low intensity. Thus, after compensating for normal attenuation of the ultrasonic signals due to transmission within the body, the resultant varying intensity of reflection can be displayed in a raster scan manner to provide an actual molded or varying grey level "picture" of the surface in question.

An exemplary embodiment of the present invention will hereinafter be described in conjunction with the following drawings, wherein like numerals denote like elements and:

FIG. 2 is a schematic block diagram of a scanner system in accordance with the present invention;

DETAILED DESCRIPTION OF AN EXEMPLARY EMBODIMENT

Figures 1, 3:
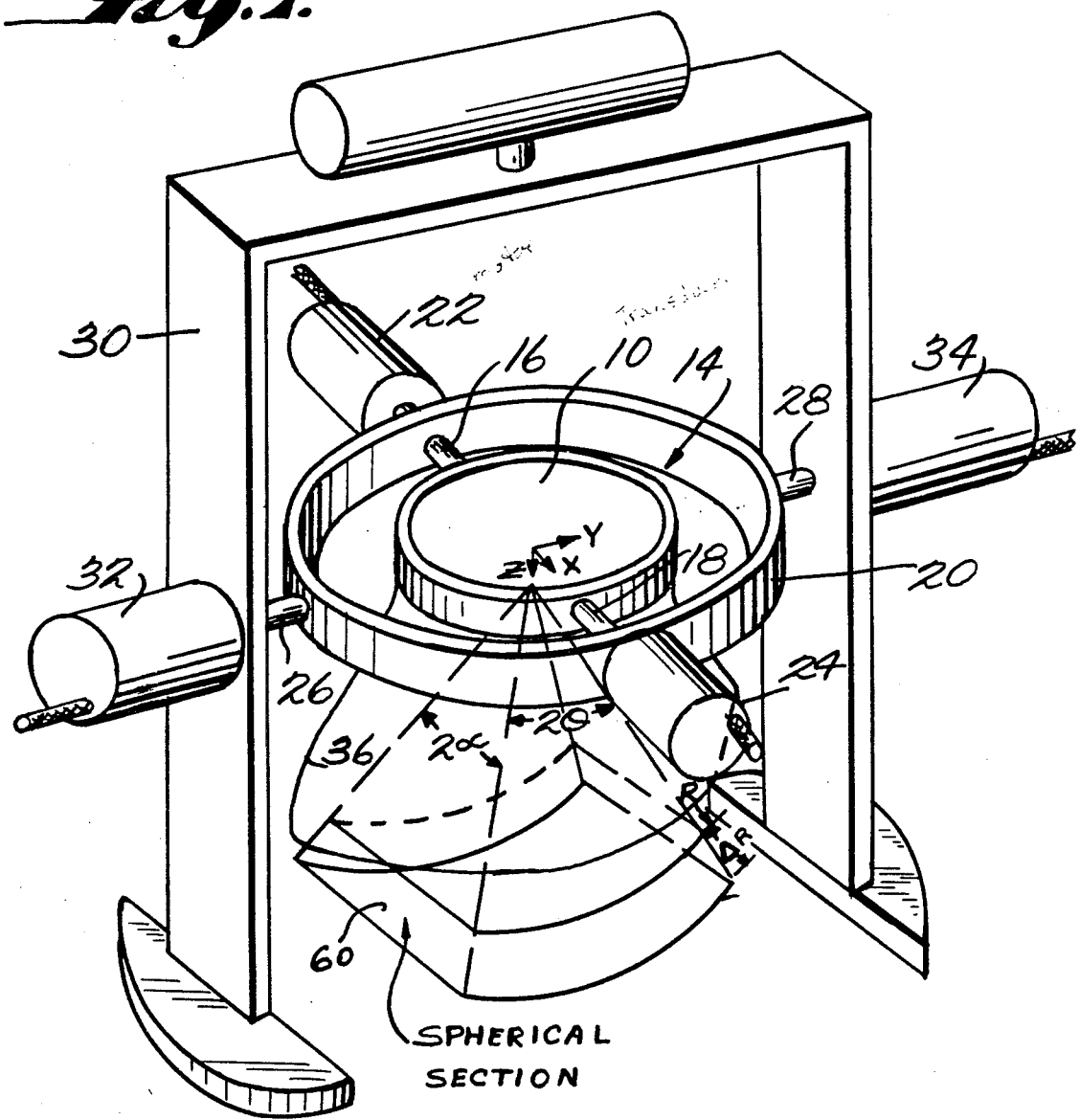
FIG. 1 is a pictorial schematic of a transducer scanning mechanism and the solid angle of volume scanned thereby.
FIG. 3 is a schematic diagram of a suitable gate control circuit.

Properly controlled phased arrays of fixed transducers may be used for scanning the ultrasonic beam. On the other hand, a mechanically scanned beam may also be employed. The particular mechanism employed for the scanning function per se is considered to be conventional, although one possible arrangement is depicted in the drawings.

Referring now to FIG. 1, a conventional ultrasonic transducer 10 is mounted in a gimbal like mechanism which provides two scanning degrees of freedom. The transducer can thus be scanned through an angle of $2\alpha$ with respect to, for example, the X-direction and through an angle of $2\theta$ with respect to, for example, the Y-direction. More specifically, transducer 10 is mounted in an inner ring 14 having shaft-like projections 16 and 18. Projections 16 and 18 are rotatably mounted in an outer ring 20, and respectively cooperate with a motor 22 of a conventional type and a sine/cosine generator 24. Sine/cosine generator 24 may be of any conventional type, but is preferably of the type comprising a light and detector system cooperating with a template affixed to projection 18. The rotation of projection 18 causes a shaped aperture in the template to progressively move into or out of a light passing relationship with the detector to produce a signal indicative of the sine or cosine of the rotational angle of projection 18. Outer ring 20 has affixed thereto shaft projections 26 and 28, which are rotatably mounted in frame or housing 30. Projections 26 and 28, respectively cooperate with a conventional motor 32 and sine/cosine generator 34.

Motor 22 provides an oscillatory motion in $\theta$ of transducer 10, while motor 32 sweeps transducer 10 in $\alpha$, to provide a raster scan of a solid angle in the body. The scanning mechanism is suitably handheld and manually positioned against the body, although mechanical positioning apparatus can, of course, be utilized. It should be appreciated that the sweeping action of transducer 10 in $\alpha$ could be manually effected by the operator rather than by use of motor 32. A water bag or gel 36 may be used to reduce attenuation in air gaps otherwise present between the transducer and body.

Referring now to FIG. 2, motors 22 and 32 are driven by suitable conventional motor drive circuitry 38, cooperating with suitable conventional timing logic 40. Cosine $\theta$ and cosine $\alpha$ signals from sine/cosine generators 23 and 34 may be utilized as feedback signals, in accordance with conventional techniques, for motor drive circuitry 38 and are also applied to timing logic 40.

Timing logic 40 may be special hardwired logic or a conventional programmed microprocessor or minicomputer. Responsive to the position signals, that is, the cosine $\theta$ and the cosine $\alpha$ signals, timing logic 40 operates to generate trigger pulses to a conventional pulser 42 such as Metrotek MP 203 type pulser. Signals from pulser 42 are applied, through a conventional T-coupler or circulator 44 to transducer 10 to effect generation of an ultrasonic pulse. Timing logic 40 generates a first trigger pulse to pulser 42 when transducer 10 is in the far upper portion of the scan as determined by the position signals, and thereafter provides trigger signals in accordance with a predetermined angular displacement within the scan. The time period between pulses is chosen in accordance with the depth of the selected interface within the body so as to permit reception of corresponding reflected signals prior to generation of the next pulse.

As is well known in the art, the distance to a reflecting interface is directly proportional to time required for the roundtrip of a pulse between the transducer and the interface. More specifically, the range distance R is equal to one-half the roundtrip transit period multiplied by the velocity of sound in the body. However, a portion of the ultrasonic pulse is reflected back to the transducer from each interface along its path. Reflections from the interfaces other than the interface of interest (hash) are thus a potential source of confusion in the display. In order to provide selectivity between the various interfaces, a range gating system is utilized. In general, range gating systems per se are well known in the radar and sonar arts. Reflections from the various interfaces are received by transducer 10 and applied through T-coupler 44 and a variable gain amplifier 46 to a gating device 48 such as an FET. Gate 48 is selectively rendered conductive for a predetermined second time period after a first time period which corresponds to the roundtrip transit time for a selected location on the near side of the area of interest. The gate is thus opened for a time period corresponding to a range R to R+$\Delta$R of distances from the transducer. Reflections from interfaces outside of that range are blocked to insure a display of only those interfaces located within the selected range.

Gate device 48 is controlled by a gate control circuit 50. A simple delay circuit for providing a range gate corresponding to a spherical surface section is shown in FIG. 3. This circuit (50a) comprises two serially connected one-shots 52 and 54, suitably Texas Instruments SN 74123 type chips. One-shot 52 is triggered by the timing logic trigger pulse used in generating the ultrasonic pulse. The duration of the output signal of one-shot 52 is made to correspond to the roundtrip distance between transducer 10 and the near side of the selected area of interest. The negative-going transition at the output of one-shot 52 is utilized to trigger one-shot 54, which produces a pulse having a duration corresponding to the thickness $\Delta$R of the selected volume. The respective durations of the one-shot output signals may be suitably controlled by the operator through potentiometers 56 and 58.

Such a gate control circuit 50a will, during the course of the scan, gate reflection signals corresponding to a portion $\Delta$R of the solid angle such as shown in FIG. 1.

Referring again to FIG. 2, the gated output signals are applied to a display means 68. Display 68 comprises a scan converter 70 and conventional CRT display 72. Scan converter 70 operates to record the gated data at the scan rate of the ultrasonic system, and then to apply such data to CRT display 72 at rates compatible with the CRT raster scan.

In accordance with one aspect of the present invention, the grey level or beam intensity of the CRT display is controlled in accordance with the amplitude of the gated signals to provide a molded or three dimensional pictorial depiction of interface surfaces within the selected portion of the scanned volume. The retro-reflection of the ultrasonic signals from the reflecting interface are proportional to the angle of incidence between the path of the ultrasonic pulse and a normal to the surface. Where the angle between the beam path and normal is small, the intensity of retro-reflection is high. When such angle of incidence is large, the retro-reflection is of low intensity. Thus, by controlling beam intensity in the CRT in accordance with the intensity of retro-reflection, an actual grey level "picture" of the interface surface is developed. The varying grey level depiction shades the otherwise two dimensional display so as to provide a three-dimensional visual effect much like the usual photograph of three-dimensional articles.

However, the ultrasonic signal naturally decreases exponentially in intensity as it passes through body tissue due to the usual attenuation. Accordingly, it is desirable to provide compensation for such attenuation. Such compensation is accomplished in the preferred embodiment by variable gain amplifier 46. Variable gain amplifier 46 may be a Motorola MC 1350 video IF amplifier which provides a predetermined gain reduction characteristic. The gain decreases from a maximum by amounts in accordance with a predetermined function beginning at an input voltage determined by a reference voltage applied to the amplifier. A voltage $V_r$, indicative of the desired displacement R of the selected volume is utilized as the reference voltage. The gated signal or data corresponding thereto is stored in locations in the scan converter in accordance with the angles $\theta$ and $\alpha$. The scan converter generally stores the information in accordance with a Cartesian coordinate system (X, Y) wherein the X and Y positions for the data are determined as follows:

$X = S \tan \theta$ $Y = S \tan \alpha$

The value S is an arbitrary value adjusted such that the display on the CRT screen, from left to right, will be near the edge of the screen when the transducer is in its maximum angle $\theta$. For example, if the maximum angle for the transducer is $\pm 20°$, then the gain of the scan converter is adjusted such that the maximum value of X is equal to S Tan 20°. Such an adjustment will provide 1 to 1 correspondence between the transmitted ultrasonic pulses and the points on the scan converter (and, ultimately, the CRT) raster. It should be appreciated that the roundtrip transit time of the ultrasonic pulses is negligible with respect to the mechanical scanning of the transducer 10 and the display raster scanning.

It should be appreciated that the data can be digitized and stored in a high speed mass data storage or memory rather than in a scan converter. The data can then be read out of storage through an appropriate D/A converter and displayed on the CRT.

It should also be appreciated, however, that when the interface surface to be observed does not readily fit into a spherical section, the simple gate control circuit 40a may not be sufficient to adequately block unwanted reflections. For example, if spherical section 60 is considered to be a concave section and the surface of the interface to be observed were convex, the thickness of spherical section 60 would have to be relatively thick in order to encompass the interface surface. Accordingly, the display could be cluttered with indicia of interfaces other than the interface of interest but within the gated range. It is therefore desirable to contour the range gate in accordance with the particular surface to be viewed.

Assuming the range gating to begin at a distance R from the transducer, the range gate can be contoured by varying R during the course of the scan. Noting that the distance R at any instance during the scan can be expressed as a function of the cosines of $\theta$ and $\alpha$, gate control circuit 50 can be made, in accordance with one aspect of the present invention, to contour the range gate by activating gate devices at times corresponding to differing distances R in accordance with the relative disposition of the path of the ultrasonic pulses within the scanned volume.

Figure 4:
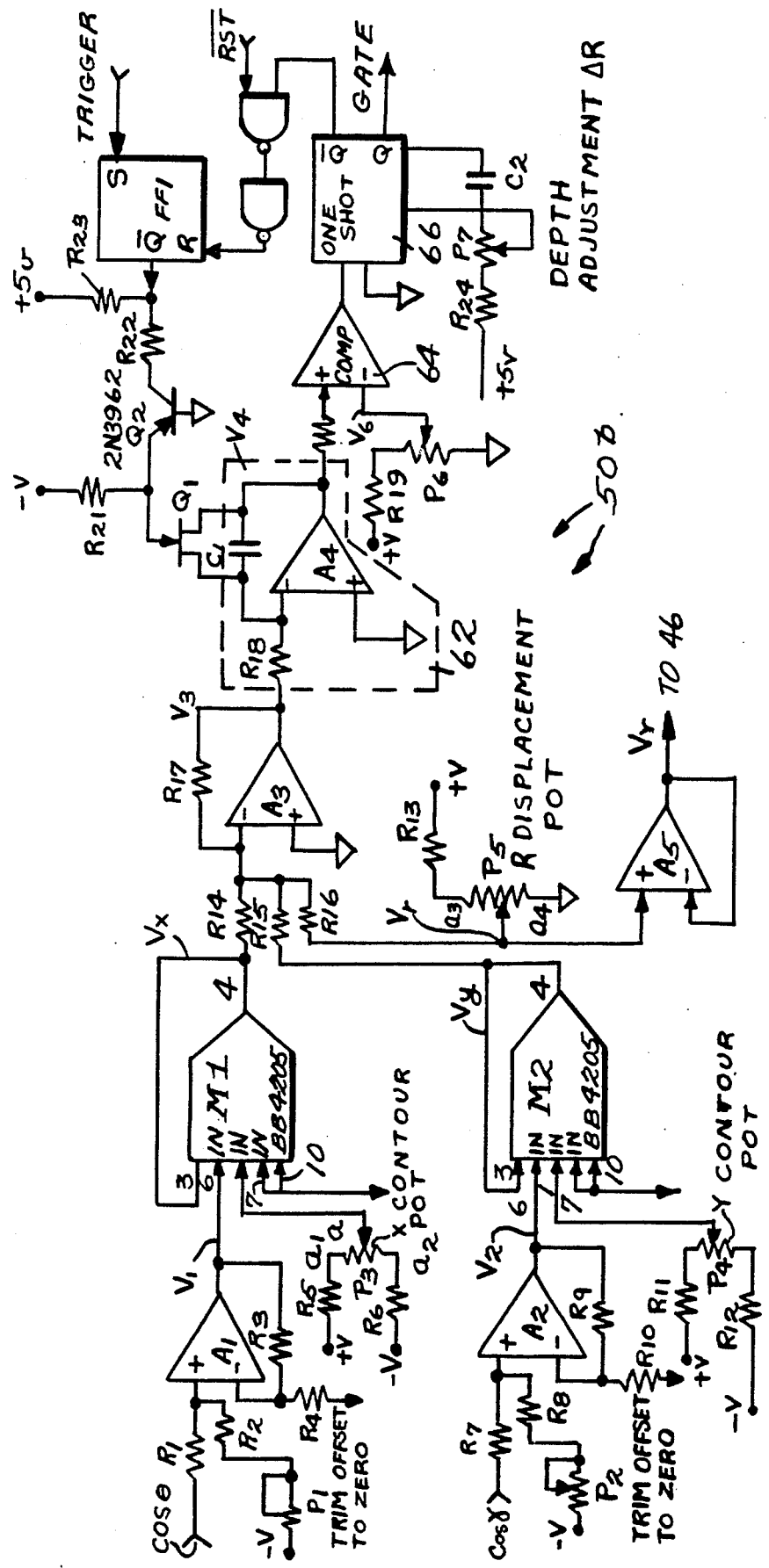
FIG. 4 is a schematic diagram of another suitable gating control circuit for effecting contour gating.
Figure 5A:
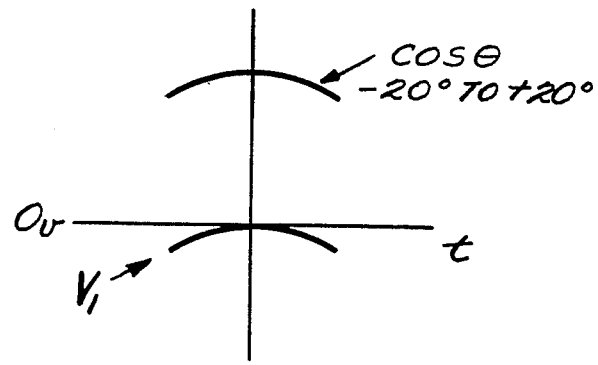
FIGS. 5a, 5b and 5c are exemplary plots versus time of various voltages $V_1$, $V_x$, and $V_3$ associated with the circuit of FIG. 4.

A suitable circuit 50b for generating control signals to gate 48 to effect a range gate that can be adjusted by the operator to follow a concave, flat, or convex surface in either the X or Y direction is shown in FIG. 4. The respective cosine signals are applied to respective amplifiers $A_1$ and $A_2$, together with voltages to adjust the respective output voltages $V_1$ and $V_2$ of amplifiers $A_1$ and $A_2$ to provide a zero voltage at 0°. An example of a typical cosine $\theta$ voltage function over ±20° scan is shown in FIG. 5(a), along with the corresponding adjusted voltage $V_1$. Voltages $V_1$ and $V_2$ are respectively applied to one input terminal of suitable multiplier modules $M_1$ and $M_2$, such as Burr Brown BB 4205 type multipliers. Multipliers $M_1$ and $M_2$ also receive at the other input terminals, X contour voltages and Y contour voltages respectively. The X and Y contour voltages generated at levels between a positive maximum and negative minimum in accordance with potentiometers $P_3$ and $P_4$. The output voltages $V_x$ and $V_y$ of multipliers $M_1$ and $M_2$ are respectively equal to the product of the input signals divided by 10. $V_x$ and $V_y$, together with voltage $V_r$ developed by potentiometer $P_5$ (indicative of a desired R displacement), are summed by summing amplifier $A_3$. The resulting voltage $V_3$ is thus a curve, varying in accordance with $\theta$ and $\alpha$.

Figure 5B:
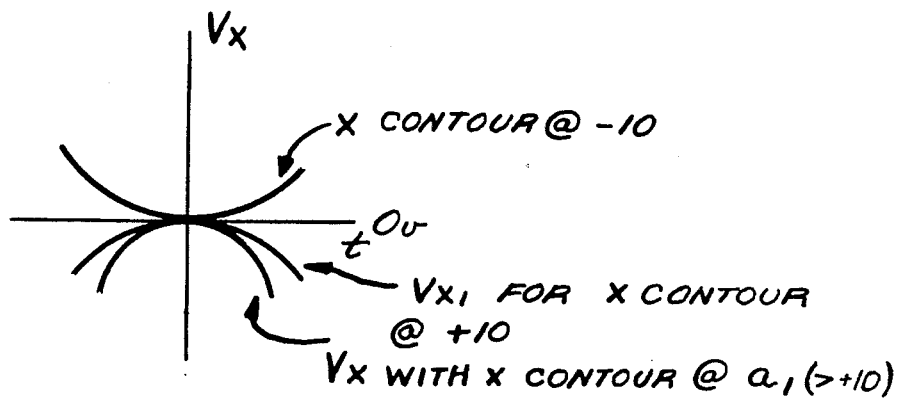

The parameters of the curve are controlled by the operator by adjusting potentiometers $P_3$, $P_4$ and $P_5$. For example, potentiometers $P_3$ and $P_4$ are respectively connected between positive and negative voltage sources. By varying the potentiometer from a center position, the respective contour voltages can be made positive or negative to provide either concave or convex curvature. As the magnitude of contour voltage becomes larger, the voltage waveform will become more curved with the cosine of the respective associated angle. Such a contour adjustment of $V_x$ is illustrated in FIG. 5b.

Figure 5C:
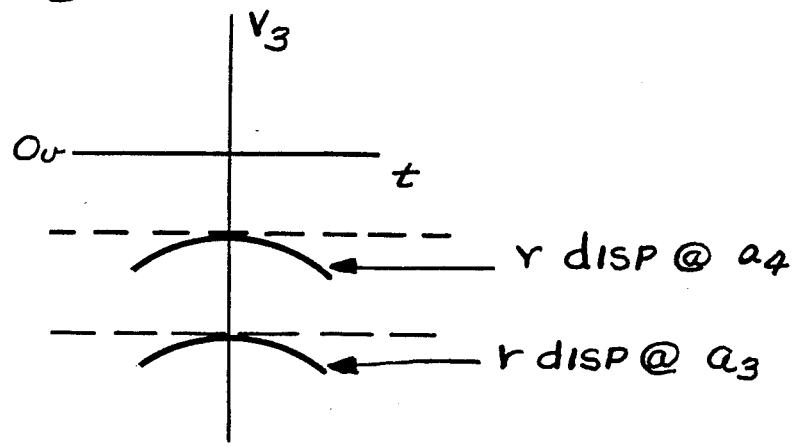

The R displacement voltage $V_r$ corresponds to the estimated distance to the interface of interest. As illustrated in FIG. 5c, the R displacement voltage $V_r$, in effect, sets the DC level of voltage $V_3$ where $\theta$ and $\alpha$ are both zero, i.e., the maximum or minimum of $V_3$.

The voltage $V_3$ is applied to an integrator 62 comprising an amplifier $A_4$, resistor $R_{18}$ and capacitor $C_1$. The output of integrator 62, $V_4$, is given by the following equation:

$$V_4 = (1/C_1) \int (V_3/R_{18}) dt.$$

However, the controlled integration period is very short such that $V_3$ varies only slightly during the integration and can be considered a constant. Accordingly, $V_4$ may be expressed:

$$V_4 = [V_3/(C_1 R_{18})] \cdot t$$

where t is the integration time.

Voltage $V_4$ is applied to a suitable comparator 64, which also receives a variable reference voltage $V_6$ generated at potentiometer $P_6$. The voltage $V_6$ is set in accordance with the approximate distance of the interface to be viewed. Potentiometer $P_6$ can, if desired, be replaced by a switch to select various approximate starting ranges, such as 2 cm, 4 cm, etc. Comparator 64 generates a transition or pulse when $V_4$ reaches the level of $V_6$, to trigger a one-shot 66, and thereby produce a range gate pulse. The duration of the one-shot output pulse is controlled by a potentiometer $P_7$.

The integration period is initiated in accordance with the trigger pulses from timing logic 40. The trigger pulses are applied to a flip flop FF1 to set the flip flop and render nonconductive a switching device $Q_1$ shunted across integrating capacitor $C_1$. Flip flop FF1 is reset in accordance with the firing of one-shot 66 to end the integration period, discharge capacitor $C_1$ and inhibit integrator 62 until the next trigger pulse. Thus, the length of time it takes integrator $A_4$ to reach threshold level $V_6$ is generally in accordance with the equation, $A_x + B_y + C$ where $A_x$ is the x contour voltage, $B_y$ is the y contour voltage and C is $V_r$.

Thus, circuit 50b effects conduction in gate device 48 for varying time periods, corresponding to varying range gates, in accordance with the scanning motion of the transducer.

It should be appreciated that circuit 50b is only one example of many suitable contour gating control circuits. Suitably programmed digital circuits could also be used. In practice, the predetermined function provided by the contour gating control circuit is chosen in accordance with the general expected shape of the objects to be viewed.

It should be noted that while the various conductors shown interconnecting the elements of the drawings are shown in single lines, they are not shown in a limiting sense and may comprise plural connections as is understood in the art. Further, it will be understood that the above description of one exemplary embodiment of the present invention is for illustrative purposes only. The invention is not limited to the specific form shown, and many modifications may be made in the specific design and arrangement of elements without departing from the spirit or scope of the invention as defined in the appended claims.

What is claimed is:

1. An ultrasonic scanner system developing a two-dimensional display of multi-valued signals representative of the varying intensities of ultrasonic signals reflected from three dimensional interfaces within a body, which intensities vary as a function of the angle of incidence of incident ultrasonic signals, said system comprising:

an ultrasonic transceiver for generating ultrasonic signals, directing said ultrasonic signals into said body along a path of predetermined disposition, and generating electrical output signals indicative of ultrasonic signals reflected back to said transceiver from said reflective interfaces;

said transceiver including scanning means for scanning said path of predetermined disposition and thus said ultrasonic signals through a predetermined volume within said body;

position means generating position signals indicative of the relative instantaneous dispositions of said ultrasonic signal path;

gating means, responsive to said position signals and to said transceiver output signals, for selectively passing only output signals representative of reflections from interfaces located within a substantial range of distances varying within predetermined minimum and maximum distances from said transceiver, which distances at any given time are a function of the instantaneous relative disposition of said ultrasonic signal path thereby generating gated output signals representative of reflections from interfaces within a selected volume having a predetermined contour; and display means, responsive to said gated output signals and to said position signals providing a two-dimensional display of multi-valued signals having more than 2 values and directly representative of and correlated to the corresponding varying intensities of ultrasonic signals reflected from the three-dimensional interface surfaces in said contoured volume so as to directly present a shaded two-dimensional depiction of said three dimensional interface surfaces.

2. The system of claim 1 wherein said display means includes a cathode ray tube responsive to said position signals in deflecting an electron beam onto a display screen and responsive to said gated signals in modulating the intensity of said electron beam.

3. The system of claims 1 or 2 further including compensation means, connected between said transceiver and said display means, which adjusts the level of said output signals in accordance with the approximate distance traveled by the ultrasonic signals within said body thereby compensating for the attenuation of said ultrasonic signals in said body.

4. The system of claims 1 or 2, wherein said gating means comprises:

a gate device for selectively passing said output signals in response to a control signal;

first timing means generating a first timing signal representing the end of a first time period occurring after transmission of an ultrasonic signal into said body, said first time period varying in accordance with a predetermined function of said position signals; and second timing means for generating a second timing signal of predetermined duration in response to said first timing signal, said second timing signal being applied to said gate device as said control signal.

5. The system of claim 4 further comprising range control means for selectively varying said predetermined function whereby said contoured volume can be changed to accommodate a particular desired interface surface.

6. The system of claim 5 further including compensation means, connected between said transceiver and said display means, which adjusts the level of said output signals in accordance with the approximate distance traveled by the ultrasonic signals within said body thereby compensating for the attenuation of said ultrasonic signals in said body.

7. In an ultrasonic scanning system of the type comprising (a) an ultrasonic transceiver for transmitting ultrasonic signals into a body along a given path direction and for developing electrical output signals representative of ultrasonic signals reflected back to the transceiver from interfaces located along said path, (b) gating means for passing only the electrical output signals representative of reflections from interfaces within a predetermined range of distances along said path, and (c) display means responsive to output signals passed by said gating means for providing indicia representative of said interfaces, the improvement wherein:

said transceiver includes means adapted for scanning said ultrasonic signals through a predetermined volume and said system further includes position means for generating position signals indicative of the instantaneous direction of said ultrasonic signal path; and said gating means includes range control means for varying said predetermined range of distances in accordance with a predetermined function of said position signals, such that the output signals passed thereby are representative of reflections from interfaces within a selected predetermined contoured portion of the scanned volume.

8. The improved ultrasonic scanning system of claim 7 wherein said display means comprises means for generating two-dimensional pictorial representations of three-dimensional interface surfaces contained within said contoured portion of the scanned volume by displaying multi-valued visual signals representing the varying intensities of ultrasonic signals reflected from respectively corresponding portions of said surfaces.

9. The improved ultrasonic scanning system of claims 7 or 8 wherein said gating means further comprises means for selectively varying said predetermined function whereby said contoured volumed portion can be varied to accommodate a particular desired interface surface in said body.

10. The improved ultrasonic scanning system of claims 1, 2, 7 or 8 further including means for automatically effecting said scanning.

11. In an ultrasonic scanning system of the type comprising (a) an ultrasonic transducer for transmitting ultrasonic signals into a body along a given path direction and developing electrical output signals representative of ultrasonic signals reflected back to the transducer from interfaces located along said path, (b) gating means for passing only the electrical output signals representative of reflections from interfaces within a predetermined range of distances along said path, and (c) display means responsive to output signals passed by said gating means for providing indicia representative of said interfaces, the improvement wherein:

said transducer includes means adapted to scan said ultrasonic signals through a predetermined volume encompassing a predetermined interface and said system further includes position means for providing position signals indicative of the instantaneous disposition of said ultrasonic signal path within the predetermined volume;

said gating means includes means connected to receive said position signals and to change said predetermined range as a function thereof whereby only reflections from interfaces having corresponding contours are passed through said gating means; and compensation means which compensates for attenuation of said ultrasonic signals such that the amplitude of said gated signals is substantially independent of the distance to said predetermined interface whereby the signal amplitude of output signals passed by said gating means is indicative of the relative angle between the reflecting predetermined interface and said ultrasonic signal path; and said display means includes means for generating multi-valued display signals respectively corresponding to the varying amplitude of output signals passed by said gating means, and means responsive to said position signals for visually displaying said multi-valued display signals on a two-dimensional display at locations thereon respectively corresponding to the disposition of the ultrasonic signal path which caused such display signal to occur.

12. The improved ultrasonic scanning system of claim 11 wherein said display means generates shaded two-dimensional pictorial-like representations of the three-dimensional interface surfaces within the selected contoured volumed portion.

13. The system of claims 11 or 12 wherein said display means comprises a cathode ray tube with its electron beam deflected in response to said position signals and the intensity of its electron beam varied in response to the amplitude of output signals passed by said gating means.

14. In the system of claims 11 or 12, the further improvement wherein:
said gating means includes range means for varying said predetermined range of distances in accordance with a predetermined function of said position signals such that output signals passed by the gating means represent reflections from interfaces within a variably selected portion of said scanned volume.

15. The system of claim 14 wherein said display means comprises a cathode ray tube with its electron beam deflected in response to said position signals and the intensity of its electron beam varied in response to the amplitude of output signals passed by said gating means.

16. The system of claim 14 wherein said gating means further comprises means for selectively varying said predetermined function whereby the contour of the selected volume can be varied to accommodate a particular desired interface surface.

17. The system of claims 11 or 12 further including means for automatically effecting said scanning.

18. Apparatus for developing a visual representation of a predetermined internal surface in a body, said apparatus comprising:
means for transmitting an ultrasonic signal into said body along a predetermined path and for receiving ultrasonic signals retro-reflected back from surfaces encountered in said body along said path;
said means for transmitting being adapted for scanning said path throughout a predetermined volume within said body and encompassing said predetermined surface;
gating means responsive to a control signal for selectively passing signals derived from said retro-reflected ultrasonic signals to produce a gated signal representative of reflections from surfaces encountered within a predetermined range of distances located a specific distance from said means for transmitting and receiving;
means for generating position signals indicative of the instantaneous disposition of the ultrasonic signal path within said volume;
means for generating said control signal in accordance with a predetermined function of the position signals such that said gated signal represents reflections from said surfaces within a contoured portion of the scanned volume, said contoured portion being approximately fitted to the expected shape of said particular internal surface; and
display means responsive to said gated signal for providing a visual representation of said predetermined internal surfaces.

19. The apparatus of claim 18 further including:
means for varying said predetermined function whereby said contoured portion can be approximately matched to a particular surface.

20. The apparatus of claims 18 or 19 wherein said display means comprises means compensating for attenuation of said ultrasonic signals in accordance with the approximate distance traveled by the ultrasonic signals;
means generating multi-valued display signals indicative of the varying amplitude of the compensated and gated signals representing retro-reflected ultrasonic signals; and
means relating the multi-valued display signals to the position signals and producing a visual display depicting the three-dimensional internal surface being scanned.

21. The apparatus of claim 20 wherein said display means comprises a cathode ray tube connected to deflect an electron beam in response to said position signals and to vary the intensity of such electron beam in response to said multi-valued display signals.

22. A method providing a visual representation of a selected internal surface in a body comprising the steps of:
directing an ultrasonic signal into said body along a predetermined path and generating electrical reflection signals indicative of ultrasonic signals retro-reflected back from internal surfaces encountered along said path;
scanning said path through a predetermined volume of said body encompassing said selected internal surface;
generating position signals indicative of the instantaneous disposition of said ultrasonic signal path within said volume;
selectively passing said reflection signals through a gate to generate a gated signal representing retro-reflections from internal surfaces within a predetermined range of distances;
varying said predetermined range of distances in accordance with a predetermined function of the position signals such that said gated signal represents retro-reflections from selected internal surfaces within a selected contoured portion of said scanned volume; and
generating and displaying visual indicia of said selected internal surfaces within said selected contoured portion from said gated signal.

23. A method as in claim 22 further comprising the step of compensating for the approximate distance traveled by the ultrasonic signals so that the selectively passed reflection signals are substantially independent of such distance.

24. A method as in claims 22 or 23 wherein said visual indicia are potentially multi-valued for any given location on a two-dimensinal visual display and where the value of such indicia for any given location is a function of the amplitude of retro-reflected ultrasonic signals emanating from a respectively corresponding location on the selected internal surface.

25. A method as in claim 24 wherein said predetermined function is selectively varied so as to change the contoured volume to accommodate a particular desired interface surface.

* * * * *